United States Patent [19]

Mack et al.

[11] Patent Number: Plant 6,888

[45] Date of Patent: Jun. 27, 1989

[54] CHRYSANTHEMUM PLANT NAMED BRAVO

[75] Inventors: Grace H. Mack, 108 Wahackme Rd., New Canaan, Conn. 06840; Cornelis P. VandenBerg, Salinas, Calif.

[73] Assignee: Grace H. Mack, New Canaan, Conn.

[21] Appl. No.: 97,584

[22] Filed: Sep. 16, 1987

[51] Int. Cl.[4] ..... A01H 5/04

[52] U.S. Cl. ..... Plt./82

[58] Field of Search ..... Plt./82

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Bravo particularly characterized by its flat capitulum form; decorative capitulum type; red ray floret color; diameter across face of capitulum of up to 4.5 cm at maturity; short plant height with spreading and prolific branching pattern; average natural season flower date of August 23 in Salinas, Calif. and September 25 in Hightstown, N.J.; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of Chrysanthemum, botanically known as *Dendranthema grandiflora* Ramat., and referred to by the cultivar name Bravo.

Bravo, identified as 83M02003, was originated from a cross made by Grace H. Mack in a controlled breeding program in New Canaan, Conn., in 1982.

The parents of Bravo were both unnamed seedlings. Bravo was discovered and selected as one flowering plant within the progeny of the stated cross by Cornelis P. VandenBerg in October of 1983, in a controlled environment in Salinas, Calif.

The first act of asexual reproduction of Bravo was accomplished when vegetative cuttings were taken from the initial selection in January of 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Bravo are firmly fixed and are retained through successive generations of asexual reproduction.

Bravo has not been observed under all possible environmental conditions. The phenotype may vary significantly with variations in environment such as temperature, light intensity, and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July through September. Single pinching was practiced with all branches and buds retained.

The following traits have been repeatedly observed and are determined to be basic characteristics of Bravo, which, in combination, distinguish this Chrysanthemum as a new and distinct cultivar:

1. Flat capitulum form.
2. Decorative capitulum type.
3. Red ray floret color.
4. Diameter across face of capitulum up to 4.5 cm at maturity.
5. Short plant height.

6. Spreading and prolific branching pattern.
7. Average natural season flower date of August 23 in Salinas, Calif., and September 25 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Bravo, with the colors being as nearly true as possible with illustrations of this type.

Sheet 1 is a color photograph of Bravo grown as a pinched spray pot mum.

Sheet 2 is a black and white photograph of three views of the inflorescence of Bravo.

Sheet 3 is a black and white photograph showing the upper and under sides of the leaves of Bravo at three stages of development (mature, intermediate and immature).

Of the commercial cultivars known to the inventors, the most similar in comparison to Bravo is Ruby Mound, an unpatented garden mum cultivar. Reference is made to attached Chart A, which compares certain characteristics of Bravo to the same characteristics of Ruby Mound.

Similar traits are ray floret color and capitulum form and type. Bravo has more spreading and prolific branching pattern, smaller diameter across face of capitulum, shorter plant height and slightly earlier natural season flowering response in comparison with Ruby Mound. The color retention of Bravo is better than that of Ruby Mound. Ruby Mound exhibits severe bract tissue in the corolla of ray florets, while Bravo does not exhibit this trait.

In the following description, color references are made to The Royal Horticultural Society Colour Chart. The exact color for corolla of ray florets of Bravo is not represented in The R.H.S. Colour Chart, and the color values given are those closest to the actual color. The color values were determined on plant material grown in a controlled greenhouse environment in Salinas, Calif. on June 3, 1987.

Classification:

*Botanical.*—*Dendranthema grandiflora,* Ramat., cv. Bravo.

*Commercial.*—Decorative spray pot mum and garden mum.

INFLORESCENCE

A. Capitulum:

*Form.*—Flat.

*Type.*—Decorative.

*Diameter across face.*—Up to 4.5 cm at maturity.

B. Corolla of ray florets:

*Color (general tonality from a distance of three meters).*—Red.

*Color (upper surface).*—Closest to 46A.

*Color (under surface).*—180C.

*Shape.*—Flat, oblong.

C. Corolla of disc florets:

*Color (mature).*—154B to 154C.

*Color (immature).*—154A.

D. Reproductive organs:

*Androecium.*—Present on disc florets only; scant pollen.

*Gynoecium.*—Present on both ray and disc florets.

PLANT

A. General appearance:

*Height.*—Short.

*Branching pattern.*—Spreading and prolific.

B. Foliage:

*Color (upper surface).*—137A.

*Color (under surface).*—147B.

*Shape.*—Lobed and slightly serrated.

CHART A

Comparison of Bravo and Ruby Mound

| CULTIVAR | RAY FLORET COLOR | CAPITULUM FORM & TYPE | BRANCHING PATTERN |
|---|---|---|---|
| Bravo | Red | Flat Decorative | Spreading and prolific |
| Ruby Mound | Red | Flat Decorative | Upright |

| | DIAMETER ACROSS FACE OF CAPITULUM | PLANT HEIGHT | COLOR RETENTION |
|---|---|---|---|
| Bravo | Up to 4.5 cm | Short | Good |
| Ruby Mound | Up to 6.0 cm | Medium | Poor |

| | AVERAGE NATURAL SEASON FLOWER DATE | |
|---|---|---|
| | SALINAS | HIGHTSTOWN |
| Bravo | Aug. 23 | Sept. 25 |
| Ruby Mound | Aug. 27 | Sept. 28 |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

We claim:

1. A new and distinct Chrysanthemum plant named Bravo, as described and illustrated, and particularly characterized as to uniqueness by the combined characteristics of flat capitulum form; decorative capitulum type; red ray floret color; diameter across face of capitulum of up to 4.5 cm at maturity; short plant height with spreading and prolific branching pattern; average natural season flower date of August 23 in Salinas, Calif. and September 25 in Hightstown, N.J.; uniform seven week photoperiodic flowering response to short days in photoperiodic controlled flowering programs; and durable, uniform performance in outside fall flowerings and in spring small pot flowering programs.

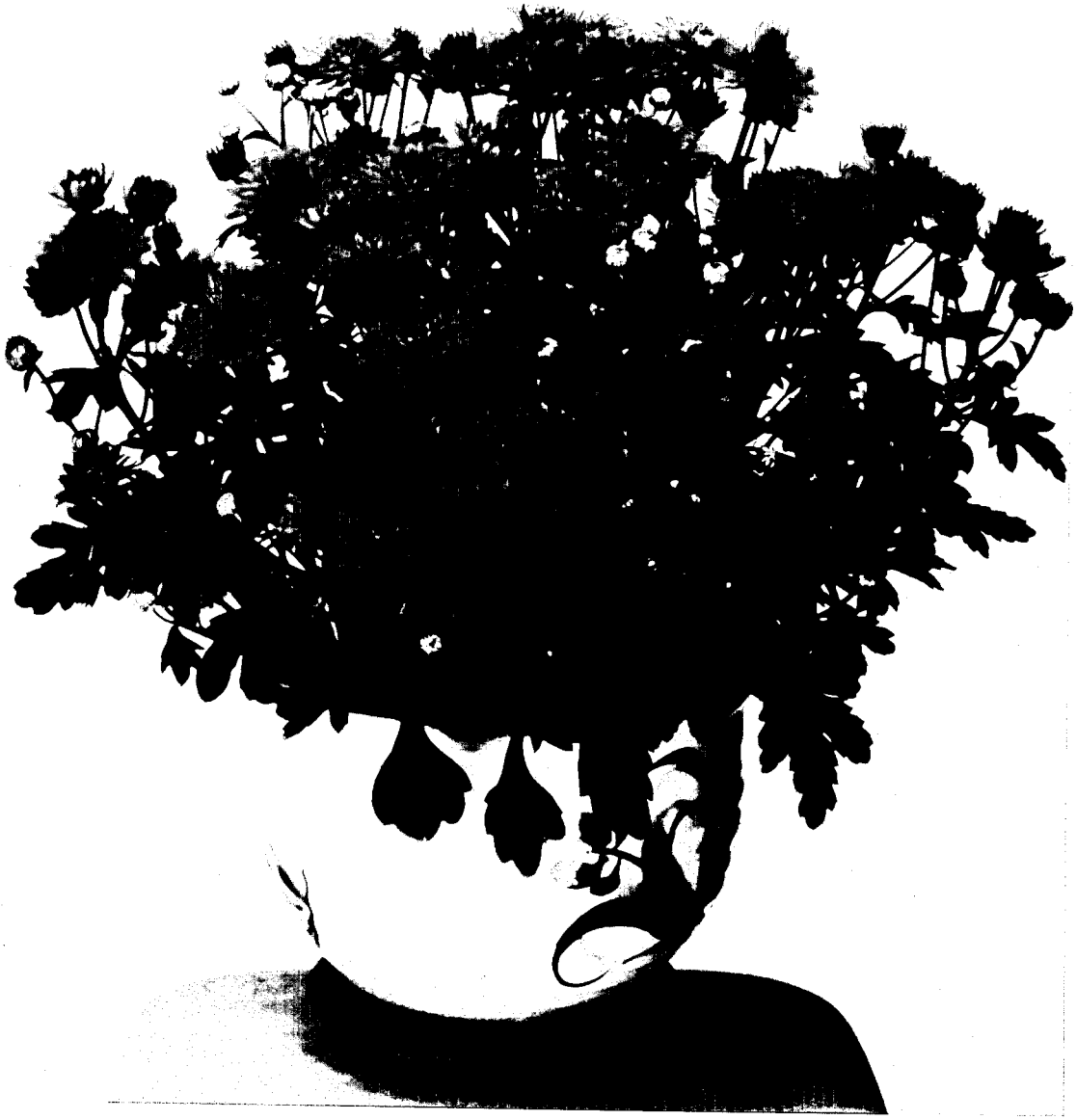

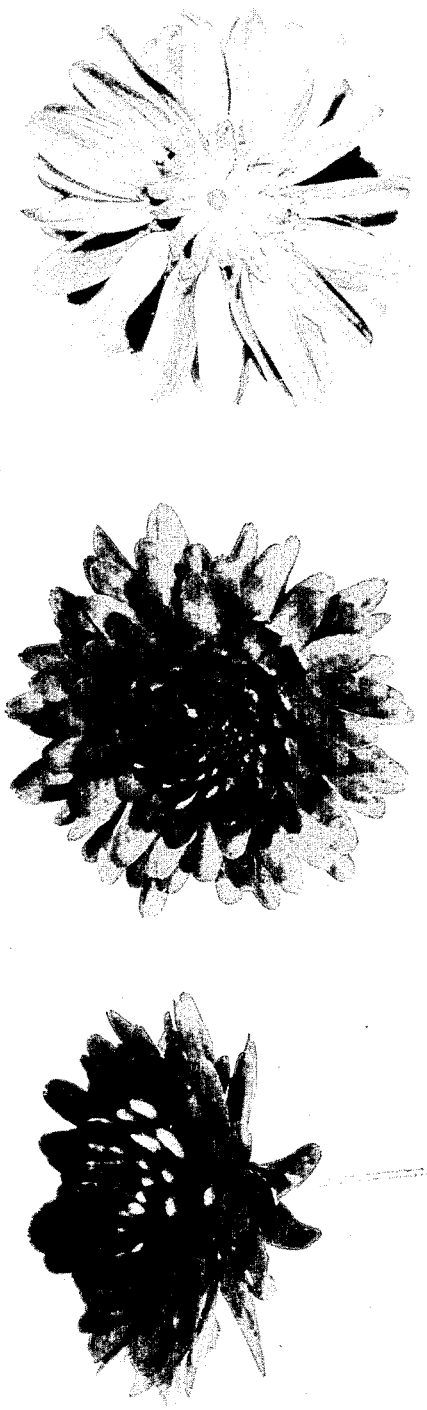

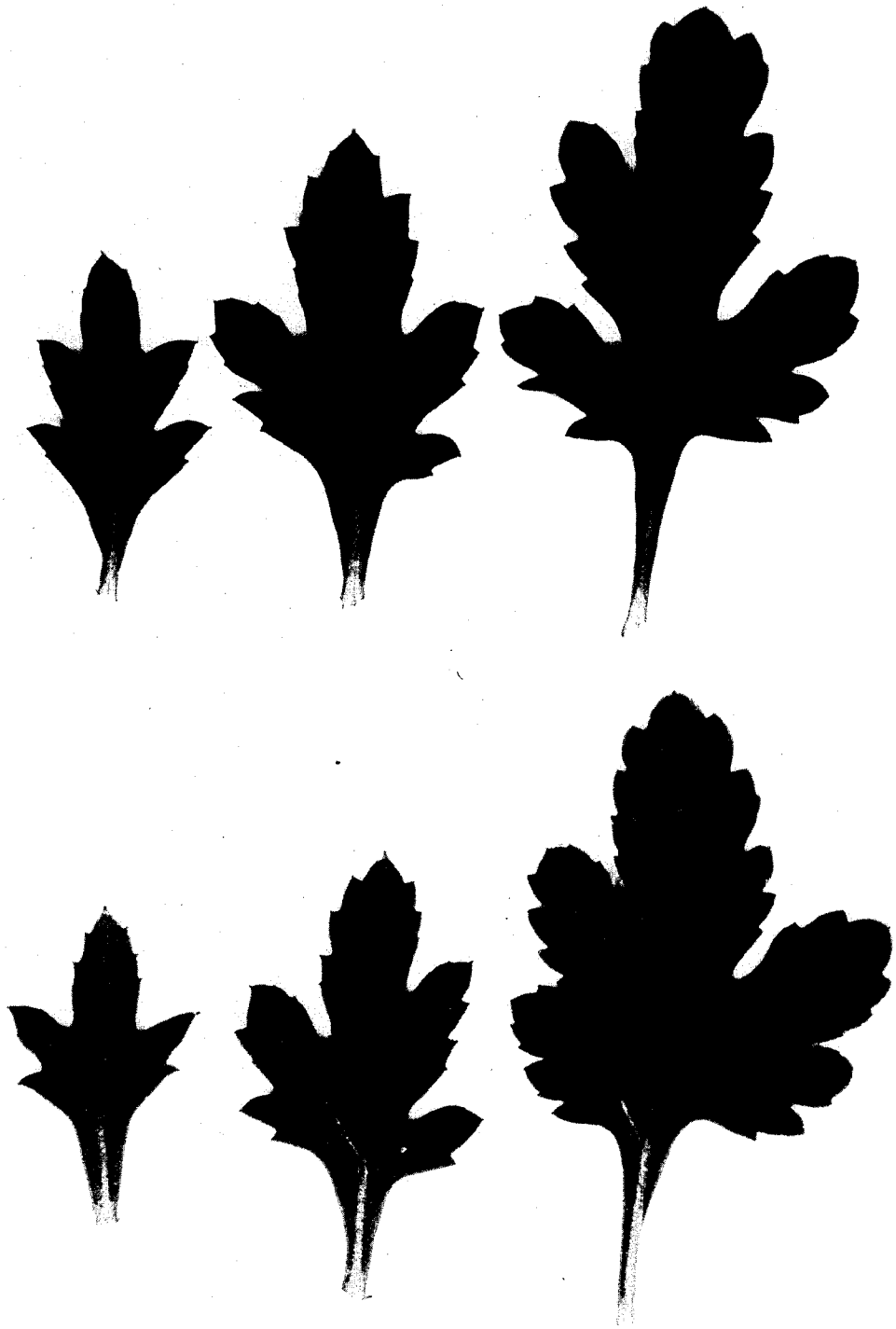

* * * * *